United States Patent [19]
Josef et al.

[11] Patent Number: 5,334,370
[45] Date of Patent: Aug. 2, 1994

[54] COMPOSITIONS OF ALKYLBENZENES IN FILM-FORMING MATERIALS FOR VISUALIZATION OF THE GASTROINTESTINAL TRACT

[75] Inventors: Kurt A. Josef, Clifton Park; Edward R. Bacon, East Greenbush; Kimberly G. Estep, Albany, all of N.Y.; Carl R. Illig, Phoenixville; Brent D. Douty, Coatesville, both of Pa.

[73] Assignee: Sterling Winthrop Inc., Malvern, Pa.

[21] Appl. No.: 13,459

[22] Filed: Feb. 4, 1993

[51] Int. Cl.$^5$ .............. A61K 49/04; C07C 69/76; C07C 22/00; C07C 25/00
[52] U.S. Cl. ................................. 424/5; 560/103; 568/470; 568/496; 570/182; 570/185
[58] Field of Search ................ 424/5; 560/103; 568/470, 496; 570/182, 185

[56] References Cited
U.S. PATENT DOCUMENTS

| | | | |
|---|---|---|---|
| 2,183,552 | 12/1939 | Driesbach | 260/650 |
| 2,186,960 | 1/1940 | Dreisbach | 260/650 |
| 3,196,080 | 7/1965 | Denny | 167/95 |
| 3,647,864 | 3/1972 | Ackerman | 260/515 P |
| 4,038,379 | 7/1977 | Elinov et al. | 424/4 |
| 4,069,306 | 1/1978 | Rothman | 424/4 |
| 4,175,544 | 11/1979 | Newton | 128/654 |
| 4,359,454 | 11/1982 | Hoffman | 424/5 |
| 4,567,280 | 1/1986 | Itatani et al. | 549/43 |
| 4,588,574 | 5/1986 | Felder et al. | 423/554 |

FOREIGN PATENT DOCUMENTS 55-127322 10/1980 Japan .

OTHER PUBLICATIONS

Kostin et al. Chem. Abs. 88:6503e (1978).
Molnar, E. J. Chem. Abs. 63.49963z (1972).
Wang et al. Yaoxne Xuebao 16(8):610–617 (1981).
James, A. M. et al. Pharm. Acta Heletiae 47:244–255 (1972).

Primary Examiner—Gary E. Hollinden
Attorney, Agent, or Firm—Arthur Rosenstein; Imre (Jim) Balogh

[57] ABSTRACT

Disclosed are x-ray contrast compositions for oral or retrograde examination of the gastrointestinal tract comprising a polymeric material capable of forming a coating on the gastrointestinal tract and an x-ray producing agent of the formula

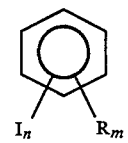

and methods for their use in diagnostic radiology of the gastrointestinal tract wherein R=$C_1$-$C_{25}$ alkyl, cycloalkyl, unsaturated allyl or halo-lower-alkyl, optionally substituted with halo, fluoro-lower-alkyl, aryl, lower-alkoxy, hydroxy, carboxy, lower-alkoxy carbonyl or lower-alkoxycarbonyloxy, $(CR_1R_2)_p$—$(CR_3=CR_4)_mQ$, or $(CR_1R_2)_p$—C≡C—Q;

$R_1$, $R_2$, $R_3$ and $R_4$ are independently H, lower-alkyl, optionally substituted with halo;

n is 1–5;

m is 1–5;

p is 1–10; and

Q is H, lower-alkyl, lower-alkenyl, lower-alkynyl, lower-alkylene, aryl, or aryl-lower alkyl.

50 Claims, No Drawings

COMPOSITIONS OF ALKYLBENZENES IN FILM-FORMING MATERIALS FOR VISUALIZATION OF THE GASTROINTESTINAL TRACT

BACKGROUND OF THE INVENTION

1. Field of the Invention

This invention relates to x-ray contrast compositions containing the contrast agents alkylbenzenes and methods for their use in diagnostic radiology of the gastrointestinal tract.

2. Reported Developments

Roentgenographic examination utilizing X-rays and computed tomography (hereinafter CT) scans of fractures and other conditions associated with the skeletal system is routinely practiced without the use of contrast agents. X-ray visualization of organs containing soft tissue, such as the gastrointestinal (hereinafter GI) tract, requires the use of contrast agents which attenuate X-ray radiation. D. P. Swanson et al in "Pharmaceuticals In Medical Imaging", 1990, MacMillan Publishing Company, provides an excellent background in medical imaging utilizing contrast agents and compositions therewith.

Roentgenographic examination of the GI tract are indicated for conditions of digestive disorders, changes in bowel habit, abdominal pain, GI bleeding and the like. Prior to radiological examination, administration of a radiopaque contrast medium is necessary to permit adequate delineation of the respective lumen or mucosal surface from surrounding soft tissues. Accordingly, a contrast medium is administered orally to visualize the mouth, pharynx, esophagus, stomach, duodenum and proximal small intestine. The contrast medium is administered rectally for examination of the distal small intestine and the colon.

The most widely used contrast agent for the visualization of the GI tract is barium sulfate administered as a suspension orally or rectally as an enema. (See, for example, U.S. Pat. Nos.: 2,659,690; 2,680,089; 3,216,900; 3,235,462; 4,038,379 and 4,120,946) Notwithstanding its relatively good contrast characteristics, negligible absorption from the GI tract following oral or rectal administration and speedy excretion from the body, barium sulfate has certain disadvantages. In the presence of intestinal fluids it lacks homogeneity and poorly adheres to mucus membranes which can result in poor X-ray images. In the colon, when administered as an enema, it flocculates and forms irregular clumps with fecal matter.

Iodinated organic compounds have also been used as GI contrast agents since the iodine atom is an effective X-ray absorber. They have the most versatility and are utilized in the widest variety of procedures. They are very absorptive of X-rays with which the iodine interacts and produce a so-called photoelectric effect which is a large magnification in contrast caused by the photons stopped in the iodine-containing medium. The magnification of contrast exceeds the level that would be expected from relative changes in density. Because of this magnification, relatively low concentrations of the contrast agent can be utilized. (For iodinated agents see, for example, U.S. Pat. Nos.: 2,786,055; 3,795,698; 2,820,814; 3,360,436; 3,574,718, 3,733,397; 4,735,795 and 5,047,228.)

The desiderata for an ideal GI contrast agent includes: good toxicological profile; the ability to fill the entire bowel/lumen and evenly coat the gut mucosa so that the presence of the bowel is detectable when the lumen is not distended; and nonirritation to the intestinal mucosa; and passage through the GI tract without producing artifacts or stimulating vigorous intestinal peristalsis.

These requirements were addressed by many investigators and their efforts resulted in great improvements over the years. The requirement of evenly coating the gut mucosa with a contrast agent to effectively cover the walls of the intestines proved to be rather difficult. Without meeting these requirements it is impossible to obtain X-ray pictures of high precision. To that end, the use of certain polymer additives were proposed as illustrated hereunder.

U.S. Pat. No. 4,069,306 discloses an X-ray contrast preparation which is said to adhere to the walls of body cavities. The preparation comprises a finely divided water-insoluble inorganic X-ray contrast agent and minute particles of a hydrophilic polymer which is insoluble in water but is water-swellable. The body cavity is supplied with such preparation suspended in water. The X-ray contrast agent is present in admixture with and/or enclosed in and/or adhered to said minute polymer particles.

U.S. Pat. No. 4,120,946 discloses a pharmaceutical composition for barium opacification of the digestive tract, comprising colloidal barium sulfate and a polyacrylamide in an aqueous vehicle. The polyacrylamide forms a viscous solution at low concentration which makes it possible to maintain the barium sulfate in suspension and at the same time permit good adherence of the preparation to the walls of the organ which it is desired to X-ray.

U.S. Pat. No. 5,019,370 discloses a biodegradable radiographic contrast medium comprising biodegradable polymeric spheres which carry a radiographically opaque element, such as iodine, bromine, samarium and erbium. The contrast medium is provided either in a dry or liquid state and may be administered intravenously, orally and intra-arterially.

While these polymeric materials greatly enhance attachment of the contrast agent used therewith to the walls of organs for better visualization thereof, they do not provide a uniform coating thereon. As such, there is still a need for an improved X-ray imaging medium that uniformly coats the soft tissues subjected to diagnostic X-ray examination.

SUMMARY OF THE INVENTION

It is the object of the present invention to provide compositions for coating the gastrointestinal tract of mammals to form an effective radiopaque coating thereon by which diagnostic examination of the GI tract may be accomplished. To that end, a thin coating is formed on the inner surface of the GI tract effected by ingesting, prior to visualization by an X-ray emitting device, a polymeric film former, which has incorporated therein an X-ray contrast agent, capable of coating the GI tract. The removal of the coating occurs as a result of the normal turnover of cells, that is, within about 24 to 48 hours. Such compositions must meet several requirements: both the X-ray contrast agent and the film former must be nontoxic; must not contain leachable or digestible components that would deleteriously affect the patient; and the composition must be capable of forming a film in the pH range of from about 5 to about 8.

The object of the present invention is achieved by a composition comprising: an X-ray contrast agent; a polymeric material which is at least partially water soluble and contains polarizable or ionizable groups; and a divalent metal ion selected from the group consisting of $Mg^{++}$, $Ca^{++}$, $Zn^{++}$ and $Ba^{++}$ which potentiates the effect of the polymeric material as a film former on the mucosa of the GI tract.

The contrast agent, polymeric film former and the divalent metal ion are incorporated in a solid or liquid media for administration to a mammal for X-ray visualization of the GI tract.

In accordance with the invention there is further provided a method for x-ray diagnostic imaging of the GI tract which comprises orally or rectally administering to the patient an effective contrast producing amount of one of the above-described x-ray contrast compositions.

The composition for radiological examination of the GI tract comprises a compound of the formula:

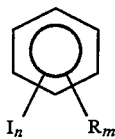

wherein

R = $C_1$–$C_{25}$ alkyl, cycloalkyl, unsaturated allyl or halo-lower-alkyl, optionally substituted with halo, fluoro-lower-alkyl, aryl, lower-alkoxy, hydroxy, carboxy, lower-alkoxy carbonyl or lower-alkoxy-carbonyloxy, $(CR_1R_2)_p$—$(CR_3\!=\!CR_4)_m Q$, or $(CR_1R_2)_p$—$C\!\equiv\!C$—$Q$;

$R_1$, $R_2$, $R_3$ and $R_4$ are independently H, lower-alkyl, optionally substituted with halo;

n is 1–5;

m is 1–5;

p is 1–10; and

Q is H, lower-alkyl, lower-alkenyl, lower-alkynyl, lower-alkylene, aryl, or aryl-lower alkyl.

As used herein, the term halogen (or halo) means fluorine, chlorine, bromine or iodine.

As used herein, the term cycloalkyl means carbocyclic rings having from three to eight ring carbon atoms including cyclopropyl, cyclobutyl, cyclopentyl, cyclohexyl and cyclooctyl which may be substituted on any ring carbon atom thereof by one or more lower-alkyl groups, lower-alkoxy groups or halogens.

As used herein the terms lower-alkyl and lower-alkoxy mean monovalent aliphatic radicals, including branched chain radicals, of from one to ten carbon atoms. Thus, the lower-alkyl moiety of such groups include, for example, methyl, ethyl, propyl, isopropyl, n-butyl, sec-butyl, t-butyl, n-pentyl, 2-methyl-3-butyl, 1-methylbutyl, 2-methylbutyl, neopentyl, n-hexyl, 1-methylpentyl, 3-methylpentyl, 1-ethylbutyl, 2-ethylbutyl, 2-hexyl, 3-hexyl, 1,1,3,3-tetramethylpentyl, 1,1-dimethyloctyl and the like.

As used herein, the term lower-alkenyl and lower-alkynyl means monovalent, unsaturated radicals including branched chain radicals of from three to ten carbon atoms and thus include 1-ethenyl, 1-(2-propenyl), 1-(2-butenyl), 1-(1-methyl-2-propenyl), 1-(4-methyl-2-pentenyl), 4,4,6-trimethyl-2-heptenyl, 1-ethynyl, 1-(2-propynyl), 1-(2-butynyl), 1-(1-methyl-2-propynyl), 1-(4-methyl-2-pentynyl) and the like.

As used herein, the term alkylene means divalent saturated radicals, including branched chain radicals of from two to ten carbon atoms having their free valences on different carbon atoms and thus includes 1,2-ethylene, 1,3-propylene, 1,4-butylene, 1-methyl-1,2-ethylene, 1,8-octylene and the like.

As used herein, the term aryl means an aromatic hydrocarbon radical having six to ten carbon atoms. The preferred aryl groups are phenyl, substituted phenyl and naphthyl substituted by from one to three, the same or different members of the group consisting of lower-alkyl, halogen, hydroxy-lower-alkyl, alkoxy-lower-alkyl and hydroxy.

The x-ray contrast compound can comprise one, two, three or more iodine atoms per molecule; preferred species contain at least two, and more preferably, at least three iodine atoms per molecule.

The solid x-ray contrast agents in particulate forms useful in the practice of the present invention can be prepared by techniques known in the art. The solid agents are comminuted to the desired size using conventional milling methods, such as airjet or fragmentation milling. We have found that an effective average particle size of less than about 100μ provides for good distribution and coating in the GI tract. As used herein, particle size refers to a number average particle size as measured by conventional techniques, such as sedimentation field flow fractionation and disk centrifugation. An effective average particle size of less than about 100μ means that at least about 90% of the particles have a weight average particle size of less than about 100μ as measured by art recognized techniques.

The polymers that were found to be suitable for forming a thin coating on the GI tract can be classified as anionic, cationic and neutral polymers, a description of which follows. U.S. Pat. No. 4,623,539, the disclosure of which is incorporated by reference, pertains to such polymers.

The contrast agent is incorporated in the polymeric material along with the divalent cation by any suitable techniques, such as by mixing, blending, precipitating or by enclosing the contrast agent into minute polymeric particles.

The contrast agent, polymeric material and divalent cation blend is then formulated for administration using physiologically acceptable carriers or excipients in a manner within the skill of the art. The contrast agent with the addition of pharmaceutically acceptable aids (such as surfactants and emulsifiers) and excipients may be suspended or partially dissolved in an aqueous medium resulting in a dispersion, solution, suspension or emulsion. Alternatively, the contrast agent, polymeric material and divalent cation may be formulated into a solid form, such as tablets or capsules.

A method for diagnostic imaging of the GI tract for use in medical procedures in accordance with this invention comprises orally or rectally administering to the mammalian patient in need of x-ray examination, an effective contrast producing amount of a con, position of the present invention. After administration, at least a portion of the GI tract containing the administered composition is exposed to x-rays to produce an x-ray image pattern corresponding to the presence of the contrast agent, then the x-ray image is visualized and interpreted using techniques known in the art.

DETAILED DESCRIPTION OF THE INVENTION

Compounds of the present invention can be made according to the schematic procedure shown or other methods using commercially available starting materials, intermediates and reagents. Starting materials, reagents and solvents can be obtained from chemical suppliers such as Aldrich, Baker and Eastman Chemical Companies, or they may be prepared by techniques known in the art.

Schematic

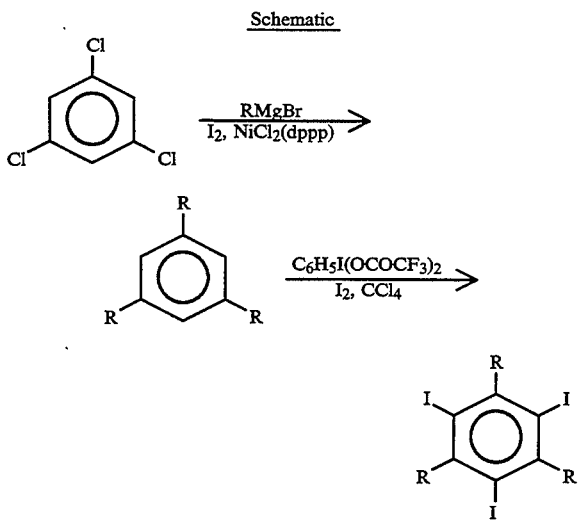

wherein R is as above described and NiCl$_2$ (dppp) represents [1,3-bis (diphenylphosphino)propane]nickel (II) chloride.

The following examples will further illustrate the compounds used in the present invention.

EXAMPLE 1

1,3,5-Tri-N-hexyl-2,4,6-triiodobenzene

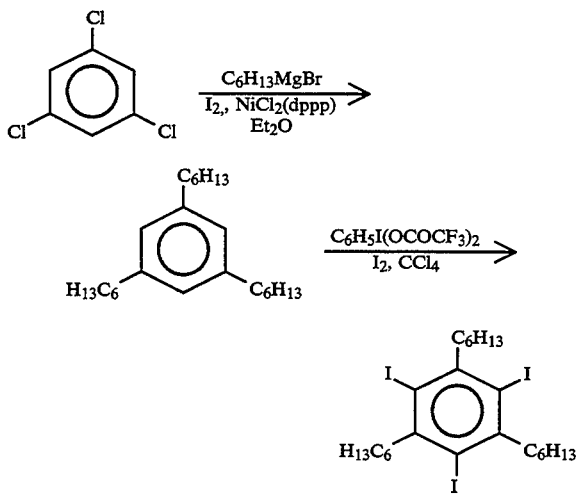

1-Bromohexane (1 ml) was added to a stirred mixture of magnesium turnings (5.88 g, 242 retool) in dry ether (25 ml) under a nitrogen atmosphere at room temperature. A crystal of iodine was added and the mixture was heated to reflux until the color faded. A solution of the remaining 1-bromohexane (33 ml, 234.8 mmol) in ether (100 ml) was added at a rate to maintain reflux. After stirring at reflux for 2 hrs, the solution was transferred by cannula to a solution of trichlorobenzene (14.2 g, 77.4 mmol) in ether (200 ml) containing [1,3-bis (diphenylphosphino) propane]nickel (II) chloride (NiCl$_2$, dppp, 0.32 g, 0.25 mol %). The solution was refluxed gently for several hours whereupon a solid began to precipitate from solution.

The reaction mixture was poured into 2000 ml of cold 1N aqueous HCl and the layers were separated. The aqueous solution was extracted with additional ether and the ether extracts were combined. The organic layer was dried over magnesium sulfate, filtered and evaporated to give 23 g of a brown oil which was then filtered through a pad of silica gel (hexanes eluent). The crude product was then pumped out under high vacuum with heating to give 19.3 g (75%) of 1,3,5-trihexylbenzene as a mobile oil. The $^1$H-NMR (300 MHz) spectral data were consistent with the desired material and the product was used in the subsequent step without further purification.

A mixture of 1,3,5-trihexylbenzene (19.3 g, 58.5 mmol), iodine (22.3 g, 87.8 mmol) and [bis(trifluoroacetoxy)iodo]benzene (40.3 g, 93.6 mmol) in 200 ml of carbon tetrachloride was stirred at room temperature overnight. The solvent was evaporated and 200 ml of 10% aqueous sodium thiosulfate was added to the residue. Dichloromethane was added and the layers were separated. The organic layer was dried over magnesium sulfate and concentrated to give an oil/solid residue mixture which was then flash chromatographed over silica gel (hexanes). The crude product was dissolved in hexanes and chilled; the precipitated solid (1,4-diiodobenzene) was removed. This crystallization procedure was repeated several times followed by silica gel chromatography (heptane elution) of the oily residue to give 4.5 g (11%) of 1,3,5-trihexyl-2,4,6-triiodobenzene as a mobile oil, after concentration and warming under high vacuum.

Title Compound $^1$H (300 MHz) and $^{13}$C (75 MHz) NMR spectra were consistent with the desired structure. Calculated for C$_{24}$H$_{39}$I$_3$: C, 40.70; H, 5.55; I, 53.75; Found: C, 40.88; H, 5.33; I, 53.78.

EXAMPLE 2

1,3,5-Triethyl-2,4,6-triiodobenzene

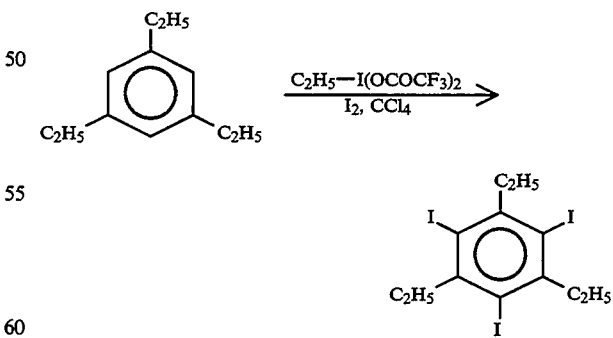

Using the procedure described for the preparation of 1,3,5-tri-N-hexyl-2,4,6-triiodobenzene, 1,3,5-triethyl-2,4,6-triiodobenzene was prepared in 56% yield from triethylbenzene (5.0 g, 31.4 mmol), [bis(trifluoroacetoxy)iodo]benzene (21.2 g, 49.2 mmol), and iodine (12.5 g, 47.2 mmol) in 50 ml of CCl$_4$. Recrystallization from cyclohexane gave 9.5 g of pure material.

Title Compound
¹H (300 MHz) and ¹³C (75 MHz) NMR spectra were consistent with the desired structure. Calculated for $C_{12}H_{15}I_3$: C, 26.69; H, 2.80; I, 70.51; Found: C, 26.84; H, 2.54; I, 70.39.

EXAMPLE 3
1,3,5-Tri-N-butyl-2,4,6-triiodobenzene

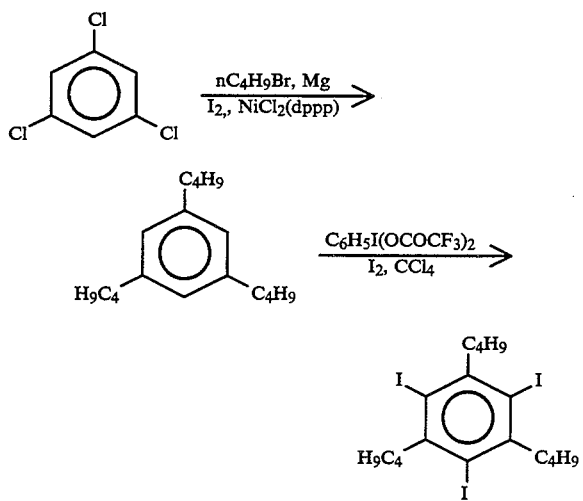

1,3,5-Tri-N-butylbenzene was prepared in 92% yield from n-butylbromide (15 ml, 140 mmol), magnesium (3.35 g, 140 mmol), trichlorobenzene (8.11 g, 44.8 mmol) and NiCl₂ (dppp) (0.2 g) in 200 ml of ether as described for the preparation of 1,3,5-tri-n-hexylbenzene. The product (10.1 g), an oil, was used directly in the next reaction without further purification. The ¹H-NMR (300 MHz) spectral data were consistent with the desired material.

Using the procedure described for the preparation of tri-N-heptyl-triiodobenzene, the tri-N-butyl derivative was prepared (0.2 g, 8% yield) from the tri-N-butyl-triiodobenzene (1 g, 4.1 mmol), [bis-(trifluoroacetoxy)iodo]benzene (3.5 g, 8.2 mmol) and iodine (1.9 g, 7.38 mmol) in 10 ml of CCl₄. Recrystallization from ethanol afforded the analytically pure product (mp. 92°–93° C.).
Title Compound
¹H (300 MHz) and ¹³C (75 MHz) NMR spectra were consistent with the desired structure. Calculated for $C_{18}H_{27}I_3$: C, 34.64; H, 4.36; I, 61.00; Found: C, 34.67; H, 4.35; I, 60.80.

EXAMPLE 4
1,3,5-Tri-(4-methylpentyl)-2,4,6-triiodobenzene

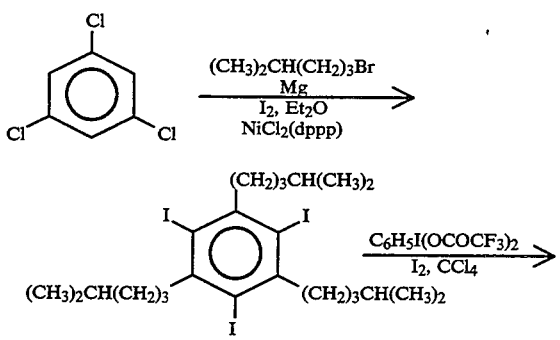

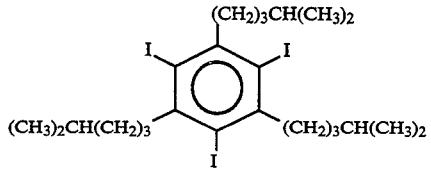

Using the procedure described for the preparation of 1,3,5-tri-N-hexyl-2,4,6-benzene, 1,3,5-tri-(4-methylpentyl) benzene was prepared in 28% yield by the reaction of isohexylbromide (10 g, 6.06 mmol), magnesium (1.5 g, 6.06 mmol), trichlorobenzene (3.52 g, 1.9 mmol) and NiCl₂ (dppp) (0.1 g) in 150 ml of ether. The ¹H-NMR (300 MHz) spectral data for the oily product (5.5 g) were consistent with the desired material which was used directly in the next step.

Using the procedure described for the preparation of 1,3,5-tri-N-butyl-2,4,6-triiodobenzene, the triisohexyl derivative was prepared in 31% yield as a crystalline solid after recrystallization from ethanol and drying under vacuum (mp. 87°–89° C.).
Title Compound
¹H (300 MHz) and ¹³C (75 MHz) NMR spectra were consistent with the desired structure. Calculated for $C_{24}H_{39}I_3$: C, 40.70; H, 5.55; I, 53.75; Found: C, 40.81; H, 5.42; I, 53.69.

EXAMPLE 5
1,3,5-Tri-N-pentyl-2,4,6-triiodobenzene

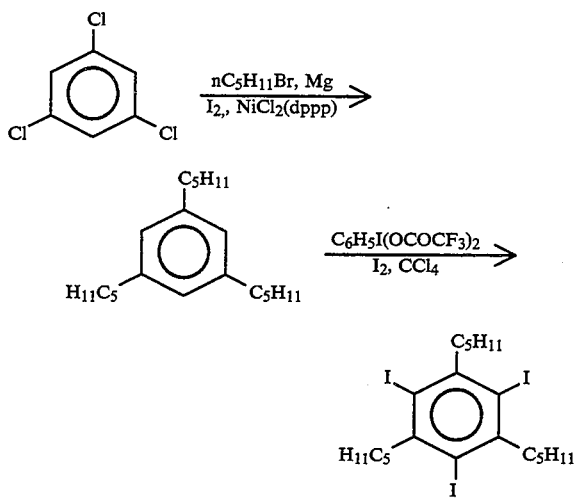

Using the procedures described for the preparation of 1,3,5-tri-N-hexylbenzene, 1,3,5-tri-N-pentylbenzene was prepared in 94% yield from n-bromopentane (20 ml, 161 mmol), magnesium (3.9 g, 161 mmol), trichlorobenzene (9.37 g, 51.5 mmol) and 0.25 g of NiCl₂ (dppp) in ether (200 ml). The product (13.8 g) was an oil and was used directly in the next step. The ¹H-NMR (300 MHz) spectral data were consistent with the desired material.

A mixture of tri-N-pentyl-triiodobenzene (5 g, 17.4 mmol), [bis(trifluoroacetoxy)iodo]benzene (14.9 g, 34.8 mmol) and iodine (7.9 g, 31.3 mmol) in 100 ml of carbon tetrachloride was stirred at room temperature overnight in a flask protected from light. The solvent was removed under vacuum and the residue was taken up in dichloromethane and washed with 10% aqueous sodium thiosulfate. The organic layer was dried over magnesium sulfate and then filtered through a short column of silica gel. The filtrate was evaporated to give a solid. The solid residue was triturated with acetonitrile and the solid material was collected. The collected solid, which contained the desired product, was then purified by column chromatography (hexanes) to give 4.7 g (40%) of the desired product (mp. 71°–72° C.).

Title Compound $^1$H (300 MHz) and $^{13}$C (75 MHz) NMR spectra were consistent with the desired structure. Calculated for $C_{21}H_{33}I_3$: C, 37.86; H, 4.99; I, 57.15; Found: C, 37.91; H, 5.00; I, 56.90.

EXAMPLE 6

1,3,5-Tri-(3-methylbutyl)-2,4,6-triiodobenzene

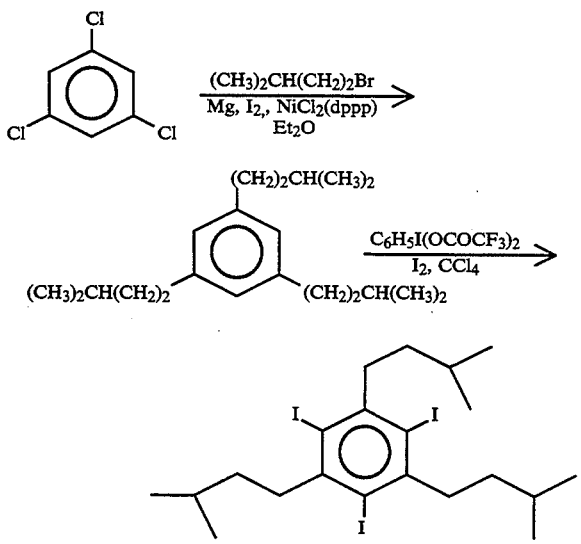

Using the procedure described for the preparation of 1,3,5-tri-N-hexylbenzene, the 1,3,5-tri-(3-methylbutyl) derivative was prepared from isopentylbromide (20 ml, 167 mmol), magnesium (4.0 g, 167 mmol), trichlorobenzene (9.7 g, 53.4 mmol) and 0.3 g NiCl$_2$ (0.25 mol %) in ether (200 ml). The desired product (10.5 g) was obtained in 22% yield as an oil after silica gel chromatography (hexanes). The $^1$H-NMR (300 MHz) spectral data were consistent with the desired product.

Using the procedure described for the preparation of 1,3,5-Tri-N-butyl-2,4,6-triiodobenzene, the triisopentyl-triiodo derivative was prepared (1% yield) as a crystalline solid after recrystallization from ethanol (mp 86°–87° C.).

Title Compound $^1$H (300 MHz) and $^{13}$C (75 MHz) NMR spectra were consistent with the desired structure. Calculated for $C_{21}H_{33}I_3$: C, 37.86; H, 4.99; I, 57.15; Found: C, 38.05; H, 5.03; I, 57.10.

EXAMPLE 7

1,3,5-Tri-N-propyl-2,4,6-triiodobenzene

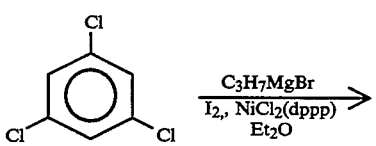

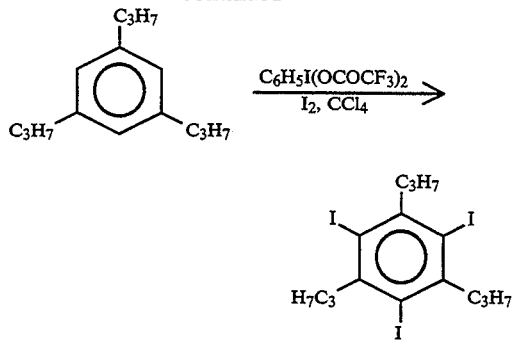

1,3,5-Tri-n-propylbenzene was prepared (5.78 g, 81%) as previously described for tri-N-hexylbenzene, from propyl bromide (10 ml, 110.1 mmol), magnesium (2.67 g, 110.1 mmol), trichlorobenzene (6.39 g, 35.2 mmol) and NiCl$_2$ (dppp) (0.15 g) in 50 ml of dry ether. The $^1$H-NMR spectral data were consistent with the desired material and the product, an oil, was used directly without further purification.

Using the procedure described for the preparation of tri-N-hexyl-triiodobenzene, the desired product was prepared (1% yield) from tri-n-propylbenzene (4.1 g, 20.1 mmol), iodine (10.2 g, 40.2 mmol) and [bis(trifluoroacetoxy)iodo]benzene (18.2 g, 42.3 mmol) in 20 ml of CCl$_4$. Recrystallization of the crude product from cyclohexane and then ethanol gave analytically pure material (mp. 95°–96° C.).

Title Compound $^1$H (300 MHz) and $^{13}$C (75 MHz) NMR spectra were consistent with the desired structure. Calculated for $C_{15}H_{21}I_3$: C, 30.95; H, 3.63; I, 65.41; Found: C, 31.03; H, 3.52; I, 65.24.

EXAMPLE 8

1,3,5-Tri-N-heptyl-2,4,6-triiodobenzene

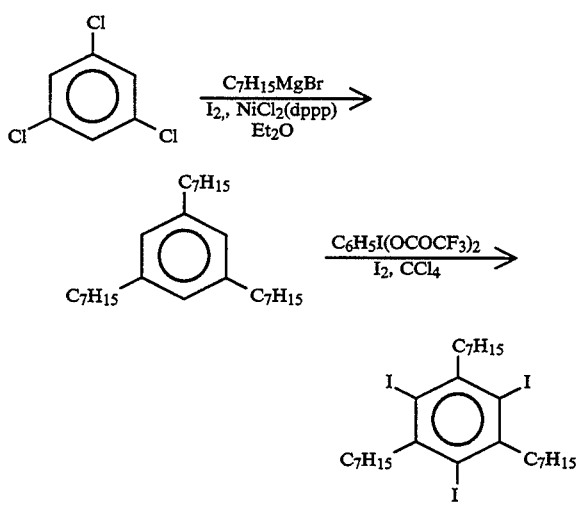

Using the procedure described for the preparation of 1,3,5-trihexylbenzene, 1,3,5-tri-N-heptylbenzene (14 g) was prepared in 93% yield as a clear oil from 1-bromoheptane (20 ml, 127 mmol) and 0.25 g of NiCl$_2$ (dppp) in dry ether (150 ml). The $^1$H-NMR (300 MHz) spectral data were consistent with the desired product which was used without further purification.

To a stirred solution of 1,3,5-triheptylbenzene (7.0 g, 18.8 mmol) in carbon tetrachloride (50 ml) was added sequentially, iodine (8.6 g, 33.8 mmol) and [bis(trifluoroacetoxy)iodo]benzene (16.2 g, 37.6 mmol) and the mixture was stirred at room temperature overnight (reaction flask was covered with aluminum foil). The solvent was recovered and the residue was taken up in dichloromethane. The organic layer was washed with 10% aqueous sodium thiosulfate, dried over magnesium sulfate and evaporated to give an oil. The oil was dissolved in hexanes and washed with acetonitrile to remove the bulk of the 1,4,-diiodobenzene present in the crude product. The product was then subjected to silica gel chromatography (hexanes) to give 4.5 g (32%) of pure tri-N-heptyltriiodobenzene and an additional 5 g of impure product. This reaction was repeated again with tri-heptylbenzene (6.32 g, 16.9 mmol), iodine (7.7 g, 30.4 mmol) and [bis(trifluoroacetoxy)iodo]benzene (14.6 g, 33.8 mmol) in carbon tetrachloride (50 ml) and the crude product was isolated as described above to give an oil which was combined with the product from the previous run. Repeated silica gel chromatography (hexanes) and warming the residue under high vacuum afforded 9.5 g, (35%) of the desired product.

Title Compound $^1$H (300 MHz) and $^{13}$C (75 MHz) NMR spectra were consistent with the desired structure. Calculated For $C_{27}H_{45}I_3$: C, 43.22; H, 6.04; I, 50.74; Found: C, 43.54; H, 6.08; I, 50.38.

EXAMPLE 9

2-(4-Iodophenyl)nonane

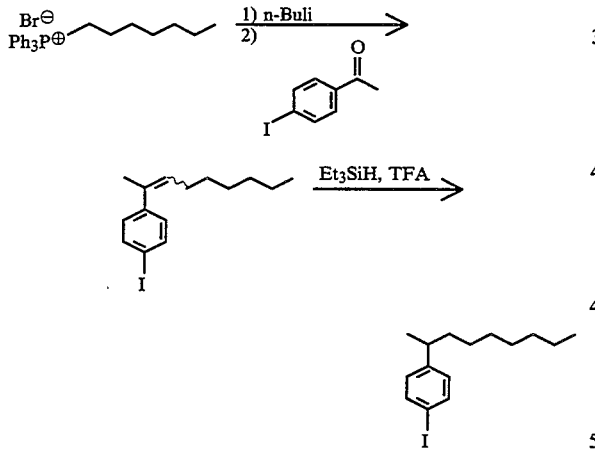

A suspension of 30.09 g (68.2 mmol) of N-heptyl-triphenylphosphonium bromide in 68 ml of dry THF was placed under nitrogen. The suspension was cooled to 0° C. and a 2.38M solution of n-BuLi in hexane (27.7 ml, 65.9 mmol) was added dropwise via syringe. The resulting deep red solution was stirred 30 min. at 0° C. before a solution of 12.00 g (45.5 mmol) of 4-iodoacetophenone in 45 ml of dry THF was added dropwise. The resulting solution was allowed to warm to room temperature at which time an orange suspension formed. The suspension was stirred at room temperature for 72 hrs and was cooled to 0° C. A solution of saturated NH$_4$Cl in water was added dropwise until the suspension was colorless. The mixture was partitioned between 300 ml of water and 250 ml of ethyl acetate. The ethyl acetate layer was then washed with brine (50 ml), dried over Na$_2$SO$_4$ and concentrated in vacuo to yield an oily tan solid. The solid was washed with hexane (200 ml), filtered and the filtrate was concentrated in vacuo to yield 12.26 g of yellow oil. The oil was purified by flash chromatography on 367 g of silica gel with 2.5% ethyl acetate/hexane as eluent. The first 525 ml to elute contained nothing while the pure product eluted with the next 500 ml. Concentration in vacuo afforded 9.98 g (67%) of product isomers as a slightly yellow tinted oil. $^1$H-NMR (300 MHz) spectral data were consistent with the desired structure.

A mixture of 12.50 g (38.08 mmol) of 2-(4-iodophenyl)-2-nonene and 6.42 g (55.2 mmol) of triethylsilane was cooled to 0° C. Trifluoroacetic acid (13.03 g, 114.2 mmol) was added dropwise and the resulting mixture was stirred at room temperature for 22 hrs before it was heated to reflux for 30 min. The mixture was cooled and partitioned between 200 ml hexanes and 100 ml of 10% K$_2$CO$_3$ in water. The hexane layer was washed with brine (50 ml) and dried over Na$_2$SO$_4$. The colorless solution was concentrated in vacuo to 12.31 g of a colorless oil The oil was purified by flash chromatography on 370 g of silica gel with hexane as the eluent. Concentration in vacuo afforded 11.45 g (91%) of product as a mobile colorless oil.

Title Compound $^1$H (300 MHz) and $^{13}$C (75 MHz) NMR spectra were consistent with the desired structure. FAB/MS: M+330. Calculated for $C_{15}H_{23}I$: C, 54.55; H, 7.02. Found: C, 55.00, H, 7.02.

EXAMPLES 10 & 11

9-(p-Iodophenyl)-10-undecenoic acid, ethyl ester and (E)-11-(p-iodophenyl)-9-undecenoic acid, ethyl ester

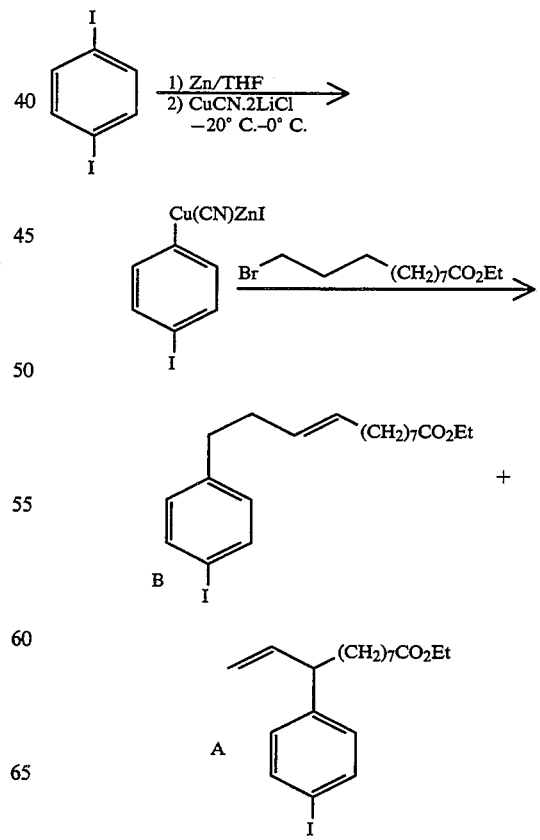

A 50 ml round bottom flask was charged with 213 mg (30.7 mmol) of freshly-cut lithium wire and 3.99 g (31.1 mmol) of naphthalene. Dry THF (15 ml) was added, and the resulting dark green mixture was stirred at room temperature for 2 hrs. A solution of 2.09 g (15.3 mmol) of $ZnCl_2$ in 15 ml THF was then added over 15 min., and the resulting suspension of active zinc was stirred an additional 15 min. The p-diiodobenzene (3.37 g, 10.2 mmol) was then added in one portion, and the mixture was allowed to stir at room temperature for 18 hrs. Stirring was stopped, and after the excess zinc had settled, the dark brown supernatent solution was transferred via cannula to a 100 ml round bottom flask and cooled to $-20°$ C. A solution of 910 mg (21.4 mmol) of LiCl and 950 mg (10.6 mmol) of CuCN in 15 ml THF was added over 3 min. and, after stirring an additional 5 min., the mixture was warmed to $0°$ C. for 20 min. and re-cooled to $-20°$ C. Ethyl 11-bromo-9-undecenoate (2.33 g, 8.01 mmol) was added dropwise and after stirring for 20 min., the reaction mixture was placed in an ice bath and was allowed to warm to room temperature as stirring was continued for 18 hrs. The reaction mixture was then poured into 20 ml saturated $NH_4Cl$ solution, and 50 ml of ether was added. The layers were separated and the aqueous phase was extracted with ether, decanting the organic layers away from the brown residue which forms. Water (100 ml) was added to the combined organic phases and, after removing the white precipitate by filtration, the layers were separated and the organic phase was dried ($MgSO_4$) and concentrated to a yellow oil. The crude product was chromatographed on silica gel using hexanes to elute the naphthalene, then 10% ethyl acetate/hexanes to afford 2.70 g (81%) of a pale yellow oil which was shown by GC and NMR spectral analysis to be a 3:2 mixture of A:B, plus an undetermined amount (40%) of des-iodo products. The latter were removed by distillation (bp $80°-145°$ C., 0.25 mm Hg). Analytical samples of A and B were obtained by chromatographing a portion of the pot residue on silica gel impregnated with 10% $AgNO_3$ using gradient elution (2%–5% ethyl acetate/hexanes).

Title Compound $^1$H (300 MHz) and $^{13}$C (75 MHz) NMR spectra were consistent with the desired structure. MS: MH+ 415. Calculated: C, 55.08; H, 6.57; I, 30.63. Found for $C_{19}H_{27}IO_2$: C, 55.16; H, 6.43, I, 30.25.

Title Compound $^1$H (300 MHz) and $^{13}$C (75 MHz) NMR spectra were consistent with the desired structure; however, the compound is unstable and will decompose within 30 days. MS: MH+ 415. Calculated for $C_{19}H_{27}IO_2$: C, 55.08; H, 6.57, I, 30.63. Found: C, 54.14; H, 6.48; I, 28.45.

Compositions of the Present Invention

The contrast agents may be formulated for administration using physiologically acceptable carriers or excipients in a manner within the skill of the art. The compounds with the addition of pharmaceutically acceptable aids (such as surfactants and emulsifiers) and excipients may be suspended or partially dissolved in an aqueous medium resulting in a dispersion, solution or suspension. However, the oily contrast agents are preferably made into emulsions.

Compositions of the present invention comprise the following pharmaceutically acceptable components based on % w/v:

| | |
|---|---|
| Non-aqueous phase | 1–50 |
| Polymeric Material | 0.001–15 |
| Divalent Cation | 0.001–15 |
| Contrast Agent | 0.001–75 |
| Excipient | 0–20 |
| Aids/Surfactants/Emulsifiers) | 0.01–15 |
| Water | q.s. to 100 |

Specific Examples of the compositions of the present invention are shown in Examples 12–14.

| Example No. 12 | |
|---|---|
| 1,3,5-Tri-N-hexyl-2,4,6-triiodobenzene | 23.7% (w/v) |
| Safflower Oil | 20.0% (w/v) |
| Kappa Carrageenan | 2.0% (w/v) |
| Calcium Lactate | 2.0% (w/v) |
| Tween 21 | 2.5% (w/v) |
| Hydroxypropylmethylcellulose (4000 cPs) | 0.5% (w/v) |
| q.s. with water to 100% volume and shake | |

| Example No. 13 | |
|---|---|
| 1,3,5-Triethyl-2,4,6-triiodobenzene | 55.3% (w/v) |
| Dow Corning Medical Antifoam AF | 40.0% (w/v) |
| Pectin | 4.0% (w/v) |
| Calcium Lactate | 2.0% (w/v) |
| q.s. with water to 100% volume and shake | |

| Example No. 14 | |
|---|---|
| 1,3,5-Tri-N-butyl-2,4,6-triiodobenzene | 25.9% (w/v) |
| Simplesse ® Dietary Fat Substitute | 30.0% (w/v) |
| Heparin | 1.0% (w/v) |
| Magnesium Carbonate | 1.0% (w/v) |
| Hydroxypropylmethylcellulose (4000 cPs) | 0.5% (w/v) |
| q.s. with water to 100% volume and shake | |

The nonaqueous phase comprises vegetable oils such as safflower oil; non-metabolizing fat substituents, such as Simplesse; fluorinated hydrocarbons, such as perfluorodecalin; mineral oil and simethicone.

Excipients advantageously used in the formulations include viscosity mediating and stabilizing agents, such as microcrystalline cellulose, ethylcellulose, hydroxypropyl methylcellulose and gum arabic. Physiologically acceptable substances may also be included, such as sodium citrate, sodium chloride, therapeutic substances, antacid substances and flavoring agents. The inclusion of antimicrobial/antiseptic agents such as methyl parahydroxybenzoate, ethyl parahydroxybenzoate, propyl parahydroxybenzoate, benzoic acid or sorbic acid may also be desirable in some formulations.

As known by those skilled in the art, surfactants or emulsifiers can reduce the interfacial tension between two immiscible phases, i.e., oil-in-aqueous medium. These agents can be used alone or in combination with other emulsifying agents and surfactants. For example, Dow Corning Medical Antifoam AF, which is a composition of 30% w/v polydimethylsiloxane simethicone and silica aerogel, 14% w/v stearate emulsifiers and 0.075% w/v sorbic acid, the balance being water, may be used by itself. Intralipid, which is an emulsion of fatty acids needs the presence of a suspending agent for it to form an acceptable emulsion with contrast agents of the present invention. The amount of such surfactants may be in the range of from 0.01 to 15% w/v of the aqueous formulations, although the amount, in general, is kept as low as possible, preferably in the range of 0.05 to 5% w/v. The surface active agents may be cationic, anionic, nonionic, zwitterionic or a mixture of two or more of these agents.

Suitable cationic surfactants include cetyl trimethyl ammonium bromide. Suitable anionic agents include sodium lauryl sulphate, sodium heptadecyl sulphate, alkyl benzenesulphonic acids and salts thereof, sodium butylnaphthalene sulfonate, and sulphosuccinates. Zwitterionic surface active agents are substances that when dissolved in water they behave as diprotic acids and, as they ionize, they behave both as a weak base and a weak acid. Since the two charges on the molecule balance each other out the molecules act as neutral molecules. The pH at which the zwitterion concentration is maximum is known as the isoelectric point. Compounds, such as certain amino acids having an isoelectric point at the desired pH of the formulations of the present invention are useful in practicing the present invention.

In preparing the formulations of the present invention we prefer to use nonionic emulsifiers or surface active agents which, similarly to the nonionic contrast agents, possess a superior toxicological profile to that of anionic, cationic or zwitterionic agents. In the nonionic emulsifying agents the proportions of hydrophilic and hydrophobic groups are about evenly balanced. They differ from anionic and cationic surfactants by the absence of charge on the molecule and, for that reason, are generally less of an irritant than the cationic or anionic surfactants. Nonionic surfactants include carboxylic esters, carboxylic amides, ethoxylated alkylphenols and ethoxylated aliphatic alcohols.

One particular type of carboxylic ester nonionic surface active agents are the partial, for example mono-, esters formed by the reaction of fatty and resin acids, for example of about 8 to about 18 carbon atoms, with polyhydric alcohols, for example glycerol, glycols such as mono-, di-, tetra- and hexaethylene glycol, sorbitan, and the like; and similar compounds formed by the direct addition of varying molar ratios of ethylene oxide to the hydroxy group of fatty acids.

Another type of carboxylic esters is the condensation products of fatty and resin partial acids, for example mono-, esters ethylene oxide, such as fatty or resin acid esters of polyoxyethylene sorbitan and sorbitol, for example polyoxyethylene sorbitan, monotall oil esters. These may contain, for example, from about 3 to about 80 oxyethylene units per molecule and fatty or resin acid groups of from about 8 to about 18 carbon atoms. Examples of naturally occurring fatty acid mixtures which may be used are those from coconut oil and tallow while examples of single fatty acids are dodecanoic acid and oleic acid.

Carboxylic amide nonionic surface active agents are the ammonia, monoethylamines and diethylamine amides of fatty acids having an acyl chain of from about 8 to about 18 carbon atoms.

The ethoxylated alkylphenol nonionic surface active agents include various polyethylene oxide condensates of alkylphenols, especially the condensation products of monoalkylphenols or dialkylphenols wherein the alkyl group contains about 6 to about 12 carbon atoms in either branched chain or particularly straight chain configuration, for example, octyl cresol, octyl phenol or nonyl phenol, with ethylene oxide, said ethylene oxide being present in amounts equal to from about 5 to about 25 moles of ethylene oxide per mole of alkylphenol.

Ethoxylated aliphatic alcohol nonionic surface active agents include the condensation products of aliphatic alcohols having from about 8 to 18 carbon atoms in either straight chain or branched chain configuration, for example oleyl or cetyl alcohol, with ethylene oxide, said ethylene oxide being present in equal amounts from about 30 to about 60 moles of ethylene oxide per mole of alcohol.

Preferred nonionic surface active agents include: sorbitan esters (sold under the trade name Span) having the formula:

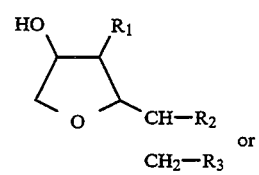

wherein
$R_1=R_2=OH$, $R_3=R$ for sorbitan monoesters,
$R_1=OH$, $R_2=R_3=R$ for sorbitan diesters,
$R_1=R_2=R_3=R$ for sorbitan triesters,
where
$R=(C_{11}H_{23})$ COO for laurate,
$(C_{17}H_{33})$ COO for oleate,
$(C_{15}H_{31})$ COO for palmitate,
$(C_{17}H_{35})$ COO for stearate.

Polyoxyethylene alkyl ethers (i.e. Brijs) having the formula:

$$CH_3(CH_2)_x(O-CH_2-CH_2)_yOH$$

where $(x+1)$ is the number of carbon atoms in the alkyl chain, typically:

| | |
|---|---|
| 12 lauryl | (dodecyl) |
| 14 myristyl | (tetradecyl) |
| 16 cetyl | (hexadecyl) |
| 18 stearyl | (octadecyl) | and y is the number of ethylene oxide groups in the hydrophilic chain, typically 10–60.

Polyethylene sorbitan fatty acid esters, sold under the trade names of Polysorbates 20, 40, 60, 65, 80 & 85.

Polyethylene stearates, such as:
poly(oxy-1,2-ethanediyl )-α-hydro-ω-hydroxyoctadecanoate;
polyethylene glycol monostearate; and
poly(oxy-1,2-ethanediyl)-α-(1-oxooctadecyl)-ω-hydroxypolyethylene glycol monostearate The film former polymeric materials used in accordance with the present invention include anionic polymers, cationic polymers and neutral polymers.

I. Anionic Polymers

The anionic polymers carry negative charges in the ionized form and are capable of binding to cell surfaces mainly by electrostatic forces. Suitable anionic polymers include the following:

$$R-O-\overset{\overset{O}{\|}}{\underset{\underset{O}{\|}}{S}}-O-M^{++},$$

-continued

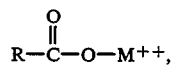

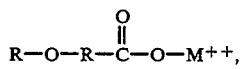

wherein
R is the polymeric chain;

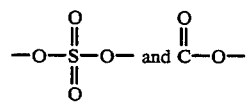

$M^{++}$ is a divalent cation.

Specific anionic polymers useful in the practice of the present invention include:

(1) Sulfated polysaccharides of the formula:

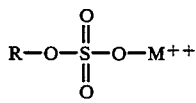

wherein
R is 3,6-anhydro-D-galactose linked through C-4 to D-galactose; (kappa carrageenan)
α-D-galactose units (1–3) linked; (lambda carrageenan)
D-galactose 3,6- anhydro-D-galactose; (iota carrageenan)
D-galactose 3,6-anhydro-L-galactose: (Agar-Agar)
D-galactose 3,6-anhydro-D-galactose; (Furcellaren)
D-glucopyranose; (Laminarin sulfate)
Galactan; and (Galactan sulfate)
Galactosamino-glucuronans (Chondroitin sulfates); and
$M^{++}$ is $Mg^{++}$, $Ca^{++}$, $Zn^{++}$, $Ba^{++}$ or mixtures thereof.

(2) Carboxylated polysaccharides of the formula:

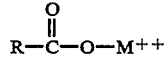

wherein
R is D-galacturonoglycan; and (Pectin)
anhydro-D-mannuronic acid and anhydro-L-guluronic acid (Algin) residues; and
$M^{++}$ is $Mg^{++}$, $Ca^{++}$, $Zn^{++}$, $Ba^{++}$ or mixtures thereof.

(3) Cellulose derivatives of the formulae:

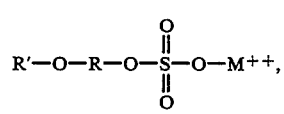

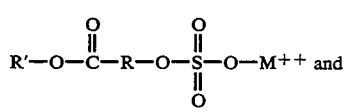

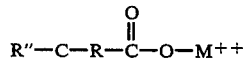

wherein
R is an anhydroglucose residue;
R' is $CH_3$, $C_2H_5$ or $C_3H_7$;
R'' is $CH_3$ or $C_2H_5$; and
$M^{++}$ is $Mg^{++}$, $Ca^{++}$, $Zn^{++}$, $Ba^{++}$ or mixtures thereof.

Examples of cellulose derivatives include: sodium ethylcellulose sulfate, sodium cellulose acetate sulfate and sodium carboxymethyl cellulose.

(4) Sulfated, sulfonated or carboxylated synthetic polymers of the formula:

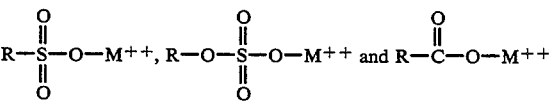

wherein
R is an aliphatic or aromatic hydrocarbon, such as polystyrene, poly(sulfon) resin or carboxylated (poly) vinyl; and
$M^{++}$ is $Mg^{++}$, $Ca^{++}$, $Zn^{++}$, $Ba^{++}$ or mixtures thereof.

II Cationic Polymers

The cationic polymers carry positive charges in the ionized form. Suitable polymers for practicing the present invention include: dermatan sulfate, keratosulfate, hyaluronic acid, heparin and chitin.

III Neutral Polymers

Neutral polymers having polarizable electrons such as oxygen, nitrogen, sulfur, fluoride, chloride, bromide and iodide are also suitable for practicing the present invention. In the presence of a cation, such as $Mg^{++}$, $Ca^{++}$, $Zn^{++}$ or $Ba^{++}$, the polymers are partially polarized thereby providing intermolecular interactions between the polymer and the intestinal wall. Examples of these polymers include:

(a) Polysaccharides, such as starch, glycogen, glucan, fructans, mannans, galactomannas, glucomannas, galactans, xylans, glycuranans, dextran and starch amylose;

(b) Cellulose derivatives, such as methylcellulose, hydroxyethylcellulose, ethylhydroxyethyl cellulose, hydroxypropyl methylcellulose and hydroxypropyl cellulose; and (c) Synthetic polymers, such as polyvinylpyrrolidone, polyvinyl alcohol and ethylene oxide polymers.

The dosages of the contrast agent used according to the method of the present invention will vary according to the precise nature of the contrast agent used. Preferably, however, the dosage should be kept as low as is consistent with achieving contrast enhanced imaging. By employing as small amount of contrast agent as possible, toxicity potential is minimized. For most contrast agents of the present invention dosages will be in the range of from about 0.1 to about 16.0 g iodine/kg body weight, preferably in the range of from about 0.5 to about 6.0 g iodine/kg of body weight, and most preferably, in the range of from about 1.2 to about 2.0 g iodine/kg body weight for regular X-ray visualization of the GI tract. For CT scanning, the contrast agents of the present invention will be in the range of from about 1 to about 600 mg iodine/kg body weight, preferably in the range of from about 20 to about 200 mg iodine/kg body weight, and most preferably in the range of from about 40 to about 80 mg iodine/kg body weight.

The concentration of the contrast agent should be in the range of from about 0.001% w/v to about 75% w/v of the formulation, preferably from about 0.05% w/v to about 50% w/v and most preferably of from about 0.1% w/v to about 20% w/v.

The concentration of the film forming polymeric material depends on the particular polymer used, however, it should be in the range of 0.001 to about 15% w/v or higher in combination with a divalent substance, such as calcium lactate, having a concentration range of 0.001 to 15% w/v. Dosage level of the polymeric material may be in the range of from about 2 to about 15 g/kg body weight or higher.

The compositions of the present invention possess very good adherence to the walls of the gastrointestinal tract by forming an essentially uniform coating thereon.

The invention having been fully described, it will be apparent to one skilled in the art that changes and modifications can be made thereto without departing from the spirit and scope thereof.

What is claimed is:

1. An x-ray contrast composition designed for depositing a thin, flexible film membrane onto the mucosal lining of the nutrient absorbing inner surface of the intestine of a patient to form a barrier between said nutrient absorbing inner surface and the content of said intestine, said flexible film membrane to remain bound to said mucosal lining until eliminated by normal cell turnover comprising based on w/v:

(a) of from about 0.001 to about 15% of a polymeric material capable of forming a film membrane on the gastrointestinal tract in the pH range of from about 5 to about 8, said polymeric material is selected from the group consisting of anionic polymers carrying negative charges in the ionized form, cationic polymers carrying positive charges in the ionized form, and neutral polymers, said neutral polymers having polarizable electrons selected from the group consisting of oxygen, nitrogen, sulfur, fluoride, chloride, bromide and iodide; in combination with (b) of from about 0.001 to about 15% of a divalent cation to potentiate the binding of said flexible film membrane to said mucosal lining selected from the group consisting of $Ca^{++}$, $Mg^{++}$, $Zn^{++}$ and $Ba^{++}$; and (c) of from about 0.001 to about 75% of an x-ray contrast producing agent having the formula, or a pharmaceutically acceptable salt thereof

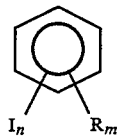

wherein

R is $C_1$–$C_{25}$ alkyl, cycloalkyl, unsaturated allyl or halo-lower-alkyl, each of which may be optionally substituted with halo, fluoro-lower-alkyl, aryl, lower-alkoxy, hydroxy, carboxy, lower-alkoxy carbonyl or lower-alkoxy-carbonyloxy, $(CR_1R_2)_p$—$(CR_3=CR_4)_mQ$, or $(CR_1R_2)_p$—$C\equiv C$—$Q$;

$R_1$, $R_2$, $R_3$ and $R_4$ are independently H, lower-alkyl, optionally substituted with halo;

n is 1–5;

m is 1–5;

p is 1–10; and

Q is H, lower-alkyl, lower-alkenyl, lower-alkynyl, lower-alkylene, aryl, or aryl-lower alkyl in a pharmaceutically acceptable carrier.

2. The composition according to claim 1 wherein said x-ray contrast agent is selected from the group consisting of: 1,3,5-tri-N-hexyl-2,4,6-triiodobenzene, 1,3,5-triethyl-2,4,6-triiodobenzene and 1,3,5-tri-N-butyl-2,4,6-triiodobenzene.

3. The composition according to claim 1 wherein said x-ray contrast agent is selected from the group consisting of: 1,3,5-tri-(4-methylpentyl)-2,4,6-triiodobenzene, 1,3,5-tri-N-pentyl-2,4,6-triiodobenzene and 1,3,5-tri-(3-methylbutyl)-2,4,6-triiodobenzene.

4. The composition according to claim 1 wherein said x-ray contrast agent is selected from the group consisting of: 1,3,5-tri-N-propyl-2,4,6-triiodobenzene, 1,3,5-tri-N-heptyl-2,4,6-triiodobenzene, 2-(4-iodophenyl)nonane, 9-(p-iodophenyl)-10-undecenoic acid, ethyl ester and (E)-11-(p-iodophenyl)-9-undecenoic acid, ethyl ester.

5. The x-ray contrast composition of claim 1 wherein said polymeric material is anionic having the formula:

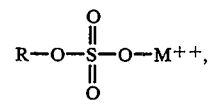

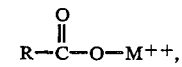

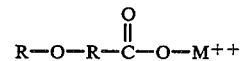

wherein

R is the polymeric chain;

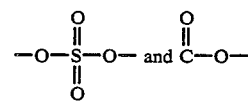

$M^{++}$ is a divalent cation.

6. The x-ray contrast composition of claim 5 wherein said anionic polymeric material is a sulfated polysaccharide having the formula:

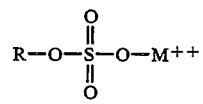

wherein

R is 3,6-anhydro-D-galactose linked through C-4 to D-galactose; (kappa carrageenan)

α-D-galactose units (1–3) linked; (lambda carrageenan)

D-galactose 3,6-anhydro-D-galactose; (iota carrageenan)
D-galactose 3,6-anhydro-L-galactose: (Agar-Agar)
D-galactose 3,6-anhydro-D-galactose; (Furcellaren)
D-glucopyranose; (Laminarin sulfate)
Galactan; and (Galactan sulfate)
Galactosamino-glucuronans (Chondroitin sulfates); and
M++ is Mg++, Ca++, Zn++, Ba++ or a mixture thereof.

7. The x-ray contrast composition of claim 5 wherein said anionic polymeric material is a carboxylated polysaccharide having the formula:

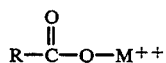

wherein
R is D-galacturonoglycan; and (Pectin)
anhydro-D-mannuronic acid and anhydro-L-guluronic acid (Algin) residues; and
M++ is Mg++, Ca++, Zn++, Ba++ or a mixture thereof.

8. The x-ray contrast con, position of claim 5 wherein said anionic polymeric material is a cellulose derivative of the formula:

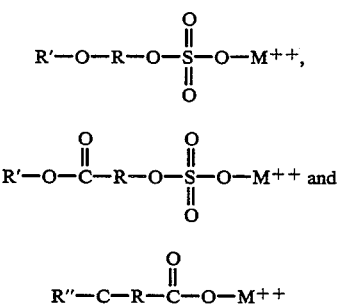

wherein
R is an anhydroglucose residue;
R' is $CH_3$, $C_2H_5$ or $C_3H_7$;
R" is $CH_3$ or $C_2H_5$; and
M++ is Mg++, Ca++, Zn++, Ba++ or a mixture thereof.

9. The x-ray contrast composition of claim 8 wherein said cellulose derivative is selected from the group consisting of sodium ethylcellulose sulfate, sodium cellulose acetate sulfate and sodium carboxymethyl cellulose.

10. The x-ray contrast composition of claim 1 wherein said anionic polymeric material is a sulfated, sulfonated or carboxylated synthetic polymer having the formula:

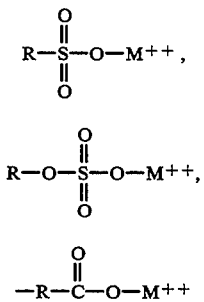

wherein
R is an aliphatic or aromatic hydrocarbon; and
M++ is Mg++, Ca++, Zn++, Ba++ or a mixture thereof.

11. The x-ray contrast composition of claim 1 wherein said polymeric material is cationic selected from the group consisting of: dermatan sulfate, keratosulfate, hyaluronic acid, heparin and chitin.

12. The x-ray contrast composition of claim 1 wherein said polymeric material is a polysaccharide.

13. The x-ray contrast composition of claim 12 wherein said polysaccharide is selected from the group consisting of starch, glycogen, glucan, fructans, mannans, galactomannans, flucomannas, galactans, xylans, glycuranans, dextran and starch amylose.

14. The x-ray contrast composition of claim 1 wherein said polymeric material is a cellulose derivative.

15. The x-ray contrast composition of claim 14 wherein said cellulose derivative is selected from the group consisting of methylcellulose, hydroxyethyl cellulose, ethylhydroxyethyl and hydroxypropyl cellulose.

16. The x-ray contrast composition of claim 1 wherein said polymeric material is polyvinylpyrrolidone, polyvinyl alcohol or an ethylene oxide polymer.

17. The x-ray contrast composition of claim 1 wherein said pharmaceutical carrier contains at least one surfactant.

18. The x-ray contrast formulation of claim 17 wherein said surfactant is cationic.

19. The x-ray contrast formulation of claim 17 wherein said surfactant is anionic.

20. The x-ray contrast formulation of claim 17 wherein said surfactant is zwitterionic.

21. The x-ray contrast formulation of claim 17 wherein said surfactant is nonionic.

22. The x-ray contrast formulation of claim 18 wherein said cationic surfactant is selected from the group consisting of cetyl trimethyl ammonium bromide and dodecyl dimethyl ammonium bromide.

23. The x-ray contrast formulation of claim 19 wherein said anionic surfactant is selected form the group consisting of sodium lauryl sulfate, sodium heptadecyl sulphate, an alkyl benzene sulphonic acid, sodium butylnaphthalene sulfonate and sulphosuccinate.

24. The x-ray contrast formulation of claim 21 wherein said nonionic surfactant is selected from the group consisting of carboxylic esters, carboxylic amides, ethoxylated alkylphenols and ethoxylated aliphatic alcohols, sorbitan esters, polyoxyethylene alkyl ethers and polyoxyethylene sorbitan fatty acid esters.

25. A method of carrying out x-ray examination of the gastrointestinal tract of a patient, said method comprises the oral or rectal administration to the patient an x-ray contrast composition designed for depositing a thin, flexible film membrane onto the mucosal lining of the nutrient absorbing inner surface of the intestine of a patient to form a barrier between said nutrient absorbing inner surface and the content of said intestine, said flexible film membrane to remain bound to said mucosal lining until eliminated by normal cell turnover comprising based on w/v:

(a) of from about 0.001 to about 15% of a polymeric material capable of forming a film membrane on the gastrointestinal tract in the pH range of from about 5 to about 8, said polymeric material is selected from the group consisting of anionic polymers carrying negative charges in the ionized form, cationic polymers carrying positive charges in the ionized form, and neutral polymers, said neutral polymers having polarizable electrons selected from the group consisting of oxygen, nitrogen, sulfur, fluoride, chloride, bromide and iodide: in combination with (b) of from about 0.001 to about 15% of a divalent cation to potentiate the binding of said flexible film membrane to said mucosal lining selected from the group consisting of $C^{++}$, $Mg^{++}$, $Zn^{++}$ and $Ba^{++}$; and (c) of from about 0.001 to about 75% of an x-ray contrast producing agent having the formula, or a pharmaceutically acceptable salt thereof

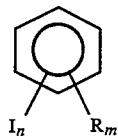

wherein

R is $C_1$–$C_{25}$ alkyl, cycloalkyl, unsaturated allyl or halo-lower-alkyl, each of which may be optionally substituted with halo, fluoro-lower-alkyl, aryl, lower-alkoxy, hydroxy, carboxy, lower-alkoxy carbonyl or lower-alkoxy-carbonyloxy, $(CR_1R_2)_p$—$(CR_3$=$CR_4)_m Q$, or $(CR_1R_2)_p$—C≡C—Q;

$R_1$, $R_2$, $R_3$ and $R_4$ are independently H, lower-alkyl, optionally substituted with halo;

n is 1–5;

m is 1–5;

p is 1–10; and

Q is H, lower-alkyl, lower-alkenyl, lower-alkynyl, lower-alkylene, aryl, or aryl-lower alkyl in a pharmaceutically acceptable carrier.

26. The method of claim 25 wherein said contrast agent is selected from the group consisting of: 1,3,5-tri-N-hexyl-2,4,6-triiodobenzene, 1,3,5-triethyl-2,4,6-triiodobenzene and 1,3,5-tri-N-butyl-2,4,6-triiodobenzene.

27. The method of claim 25 wherein said contrast agent is selected from the group consisting of: 1,3,5-tri-(4-methylpentyl)-2,4,6-triiodobenzene, 1,3,5-tri-N-pentyl-2,4,6-triiodobenzene and 1,3,5-tri-(3-methylbutyl)-2,4,6-triiodobenzene.

28. The method of claim 25 wherein said contrast agent is selected from the group consisting of: 1,3,5-tri-N-propyl-2,4,6-triiodobenzene, 1,3,5-tri-N-heptyl-2,4,6-triiodobenzene, 2-(4-iodophenyl)nonane, 9-(p-iodophenyl)-10-undecenoic acid, ethyl ester and (E)-11-(p-iodophenyl)-9-undecenoic acid, ethyl ester.

29. The method of claim 25 wherein the amount of contrast agent administered to said patient is in the range of from about 0.1 to about 16.0 g iodine/kg body weight for regular x-ray visualization of the gastrointestinal tract.

30. The method of claim 25 wherein the amount of contrast agent administered to said patient will be in the range of from about 1 to about 600 mg iodine/kg body weight for CT scan visualization of the gastrointestinal tract.

31. The method of claim 25 wherein said pharmaceutically acceptable carrier contains at least one surfactant.

32. The method of claim 31 wherein said surfactant is cationic.

33. The method of claim 31 wherein said surfactant is anionic.

34. The method of claim 31 wherein said surfactant is zwitterionic.

35. The method of claim 31 wherein said surfactant is nonionic.

36. The method of claim 32 wherein said cationic surfactant is selected from the group consisting of cetyl trimethyl ammonium bromide and dodecyl dimethyl ammonium bromide.

37. The method of claim 33 wherein said anionic surfactant is selected from the group consisting of sodium lauryl sulfate; sodium heptadecyl sulphate, an alkyl benzenesulphonic acid, sodium butylnaphthalene sulfonate and sulphosuccinates.

38. The method of claim 35 wherein said nonionic surface active agent is selected from the group consisting of carboxylic esters, carboxylic amides, ethoxylated alkylphenols and ethoxylated aliphatic alcohols, sorbitan esters, polyoxyethylene alkyl ethers and polyoxyethylene sorbitan fatty acid esters.

39. The method of claim 25 wherein said polymeric material is anionic having the formula:

$$R-O-\overset{O}{\underset{O}{\overset{\|}{S}}}-O-M^{++},$$

$$R-\overset{O}{\overset{\|}{C}}-O-M^{++},$$

$$-R-O-R-\overset{O}{\overset{\|}{C}}-O-M^{++}$$

wherein

R is the polymeric chain;

$$-O-\overset{O}{\underset{O}{\overset{\|}{S}}}-O-\ \text{and}\ \overset{O}{\overset{\|}{C}}-O-$$

$M^{++}$ is a divalent cation.

40. The method of claim 39 wherein said anionic polymeric material is a sulfated polysaccharide having the formula:

$$R-O-\overset{O}{\underset{O}{\overset{\|}{S}}}-O-M^{++}$$

wherein

R is 3,6-anhydro-D-galactose linked through C-4 to D-galactose; (kappa carrageenan)

α-D-galactose units (1–3) linked; (lambda carrageenan)

D-galactose 3,6 -anhydro-D-galactose; (iota carrageenan)

D-galactose 3,6-anhydro-L-galactose: (Agar-Agar)

D-galactose 3,6-anhydro-D-galactose; (Furcellaren)

D-glucopyranose; (Laminarin sulfate)
Galactan; and (Galactan sulfate)
Galactosamino-glucuronans (Chondroitin sulfates); and M++ is Mg++, Ca++, Zn++, Ba++ or a mixture thereof.

41. The method of claim 39 wherein said anionic polymeric material is a carboxylated polysaccharide having the formula:

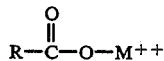

wherein
R is D-galacturonoglycan; and (Pectin)
anhydro-D-mannuronic acid
and anhydro-L-guluronic acid (Algin) residues; and
M++ is Mg++, Ca++, Zn++, Ba++ or a mixture thereof.

42. The method of claim 39 wherein said anionic polymeric material is a cellulose derivative of the formula:

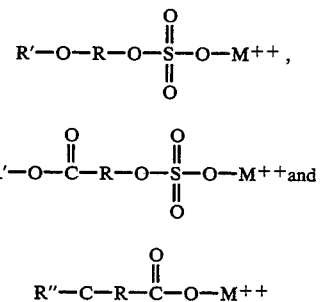

wherein
R is an anhydroglucose residue;
R' is $CH_3$, $C_2H_5$ or $C_3H_7$;
R" is $CH_3$ or $C_2H_5$; and
M++ is Mg++, Ca++, Zn++, Ba++ or a mixture thereof.

43. The method of claim 42 wherein said cellulose derivative is selected from the group consisting of sodium ethylcellulose sulfate, sodium cellulose acetate sulfate and sodium carboxymethyl cellulose.

44. The method of claim 25 wherein said anionic polymeric material is a sulfated, sulfonated or carboxylated synthetic polymer having the formula:

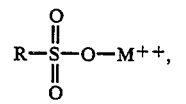

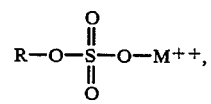

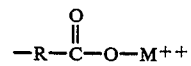

wherein
R is an aliphatic or aromatic hydrocarbon; and
M++ is Mg++, Ca++, Zn++, Ba++ or a mixture thereof.

45. The method of claim 25 wherein said polymeric material is cationic selected from the group consisting of: dermatan sulfate, keratosulfate, hyaluronic acid, heparin and chitin.

46. The method of claim 25 wherein said polymeric material is a polysaccharide.

47. The method of claim 46 wherein said polysaccharide is selected from the group consisting of starch, glycogen, glucan, fructans, mannans, galactomannans, flucomannas, galactans, xylans, glycuranans, dextran and starch amylose.

48. The method of claim 25 wherein said polymeric material is a cellulose derivative.

49. The method of claim 48 wherein said cellulose derivative is selected from the group consisting of methylcellulose, hydroxyethyl cellulose, ethylhydroxyethyl and hydroxypropyl cellulose.

50. The method of claim 25 wherein said polymeric material is polyvinylpyrrolidone, polyvinyl alcohol or an ethylene oxide polymer.

* * * * *